US011651486B2

(12) United States Patent
Rosenberg Maffia et al.

(10) Patent No.: US 11,651,486 B2
(45) Date of Patent: May 16, 2023

(54) APPARATUS FOR DETECTION OF EARLY-STAGE GLAUCOMA AND OTHER OPTIC NERVE DISEASES

(71) Applicants: Wisconsin Alumni Research Foundation, Madison, WI (US); The Royal Institution For The Advancement Of Learning/McGill University, Montreal (CA)

(72) Inventors: Peter Ari Rosenberg Maffia, Madison, WI (US); Curtis Lee Baker, Montreal (CA); Ana Leticia Ramirez Hernandez, Montreal (CA)

(73) Assignees: Wisconsin Alumni Research Foundation, Madison, WI (US); The Royal Institution for the Advancement of Learning/McGill University, Montreal (CA)

( * ) Notice: Subject to any disclaimer, the term of this patent is extended or adjusted under 35 U.S.C. 154(b) by 425 days.

(21) Appl. No.: 16/839,940

(22) Filed: Apr. 3, 2020

(65) Prior Publication Data
US 2021/0312613 A1 Oct. 7, 2021

(51) Int. Cl.
*A61B 3/02* (2006.01)
*A61B 3/10* (2006.01)
(Continued)

(52) U.S. Cl.
CPC .......... *G06T 7/0012* (2013.01); *A61B 3/0033* (2013.01); *A61B 3/0058* (2013.01); *A61B 3/14* (2013.01); *G06T 7/70* (2017.01); *A61B 3/12* (2013.01); *G06T 2207/10101* (2013.01); *G06T 2207/20182* (2013.01); *G06T 2207/30041* (2013.01)

(58) Field of Classification Search
USPC ....... 351/246, 221–224, 200, 203, 205, 206, 351/209–211, 239, 243–245
See application file for complete search history.

(56) References Cited

U.S. PATENT DOCUMENTS 6,213,956 B1 * 4/2001 Lawton .................... A61H 5/00
351/239
9,302,103 B1 * 4/2016 Nirenberg ............ A61N 1/3605
(Continued)

FOREIGN PATENT DOCUMENTS

EP 2826413 A1 1/2015
WO 9508290 A1 3/1995
(Continued)

OTHER PUBLICATIONS

Rosenberg et al. "The Y cell visual pathway implements a demodulating nonlinearity." Neuron 71, No. 2 (2011): pp. 348-361. Chicago, IL.
(Continued)

*Primary Examiner* — Dawayne Pinkney
(74) *Attorney, Agent, or Firm* — Boyle Fredrickson, S.C.

(57) ABSTRACT

A method and apparatus of early-stage detection of glaucoma and other optic nerve or retinal diseases employs dynamic images that are processed differently by Y-like cells and X-like cells to provide a sensitive detection of early Y-like cell impairment which provides early indications of glaucoma isolated from non-specific information from X-like cells.

17 Claims, 3 Drawing Sheets

(51) Int. Cl.
   *A61B 3/12*    (2006.01)
   *G06T 7/00*    (2017.01)
   *A61B 3/00*    (2006.01)
   *G06T 7/70*    (2017.01)
   *A61B 3/14*    (2006.01)

(56) References Cited

U.S. PATENT DOCUMENTS

| | | | | |
|---|---|---|---|---|
| 2004/0064065 | A1* | 4/2004 | Pescatore, Jr. | H04N 13/302 348/E13.037 |
| 2008/0004544 | A1* | 1/2008 | Caplygin | A61B 5/168 600/558 |
| 2008/0024725 | A1* | 1/2008 | Todd | A61B 3/0091 351/222 |
| 2011/0001924 | A1 | 1/2011 | Giraudet et al. | |
| 2017/0347874 | A1 | 12/2017 | Novik | |

FOREIGN PATENT DOCUMENTS

| | | | | |
|---|---|---|---|---|
| WO | WO-2005002420 | A2 * | 1/2005 | A61B 3/10 |
| WO | WO-2008013907 | A3 * | 5/2008 | A61B 3/0091 |

OTHER PUBLICATIONS

Rosenberg et al. "Subcortical representation of non-Fourier image features." Journal of Neuroscience 30, No. 6 (2010): pp. 1985-1993. Chicago, IL.
Jones et al.; "Portable Perimetry Using Eye-Tracking on a Tablet Computer—a Feasibility Assessment." Translational vision science & technology 8, No. 1 (2019): 17-17; pp. 1-11; London, UK.
Petrusca et al.; "Identification and characterization of a Y-like primate retinal ganglion cell type." Journal of Neuroscience 27, No. 41 (2007): pp. 11019-11027; California.
Prior Art; Zeiss,; "Humphrey Visual Field Analyzers"; Brochure; pp. 1-14; 2014; US.
International Search Report for PCT/US2021/022552.

* cited by examiner

APPARATUS FOR DETECTION OF EARLY-STAGE GLAUCOMA AND OTHER OPTIC NERVE DISEASES

STATEMENT REGARDING FEDERALLY SPONSORED RESEARCH OR DEVELOPMENT

CROSS REFERENCE TO RELATED APPLICATION

BACKGROUND OF THE INVENTION

The present invention relates generally to medical diagnostic equipment and in particular to an apparatus for the detection of glaucoma and other optic nerve diseases in human patients.

Glaucoma is a progressive, degenerative eye disease that is the most common cause of irreversible blindness. Glaucoma is manifested as damage to the optic nerve and, specifically, to the ganglion cells of the retina, typically from high intraocular pressure. The retinal ganglion cells first impacted include a minority of cells that have large cell bodies and large branching dendrite networks, including parasol cells and other types with analogous nonlinear properties (e.g. smooth or upsilon cells), henceforth termed Y-like cells, that provide information about more coarse spatial scales of luminance as well as fine-grain texture. In addition, there are a numerous subset, midget cells, (henceforth termed X-like cells) which have smaller cell bodies and smaller dendritic trees, and provide more sensitivity to fine detail and color. The Y-like cells are more susceptible to high intraocular pressure and thus are the earliest cells to be damaged as glaucoma progresses.

Glaucoma typically first affects the patient's peripheral vision before progressing to more central vision, and therefore may often not be noticeable to the patient until substantial and irreversible retinal damage has occurred.

The diagnosis of glaucoma is conventionally based on a combination of different clinical tests, such as direct and indirect ophthalmoscopic observation of the optic nerve head, and measurement of intraocular pressure using tonometry, which applies a slight pressure to the outer surface of the eye. Morphological assessments of possible optic nerve damage are often based on OCT (optical coherence tomography) imaging of the optic disc. While these techniques provide some information for early-stage detection, they do not estimate the reduction of the visual field and need to be accompanied by a functional assessment for a patient to be considered positive for glaucoma.

Functional or behavioral tests assess consequences for visual perception, where the SAP (Standard Automated Perimetry) is the most widely used test, in part because it is accurate and fast and thus suitable for many screening situations. In this approach, a dynamic image is positioned at different locations throughout the patient's field-of-view. The patient presses a button when the stimulus is perceptually visible to them, and a map is generated indicating portions of the patient's field where vision has been lost. However, substantial cell death, including both Y-like and X-like cells, is required before loss of peripheral vision is measurable by this test, thus the test lacks specificity and delays critical diagnostic information in early stages.

SUMMARY OF THE INVENTION

The present invention provides a sensitive, early detection of glaucoma or other eye diseases suitable for screening like SAP, while providing more sensitive detection of early-stage cell loss. This early sensitivity is possible by measuring behavioral responses that are dependent on neural signals from the Y-like cells, which are more prone to damage from glaucoma than the X-like cells, and thus provide earlier indications of cell loss. Sensitivity to Y-like cells is possible by having the patient identify perceptual attributes in specially prepared dynamic images that are primarily perceived through Y-like cells. Impairment of the patient's ability to detect, identify, or discriminate these features indicates Y-like cell loss even when X-like cells are largely unaffected.

In one embodiment, the invention provides an apparatus for glaucoma detection having an electronically controlled dynamic image display adapted for viewing by a human patient and a display driver for generating a series of dynamic images presentable on the electronically controlled display, each dynamic image providing a distinguishably different perception when received by only X-like cells than when received by Y-like cells. A patient input device is provided to receive a patient input describing orientation or direction of motion of a perceived pattern in the series of dynamic images displayed on the electronically controlled display; and a controller communicates with the display driver and electronically controlled display to:

(1) display different dynamic images at different locations within a field-of-view of a patient viewing the electronically controllable display; and (2) analyze the patient input for the different locations of each of the dynamic images to assess a loss of Y-like cells in different portions of the retina corresponding to the different visual field locations.

It is thus a feature of at least one embodiment of the invention to extract early information specific to glaucoma, by assessing functional perception that is dependent on the integrity of Y-like cells, and relatively isolated from the functioning of X-like cells that might otherwise lead an automated perimetry machine to indicate that the visual field has not been lost or compromised. Significantly, the device invention eliminates the need for the patient to make difficult assessments of spatial frequency in favor or simple assessment of orientation and/or motion determination.

The perception of the dynamic images that are selective to Y-like cell function may result from a nonlinearity in the processing of the dynamic images by the Y-like cells, and not by the X-like cells.

It is thus a feature of at least one embodiment of the invention to exploit a difference in the processing of dynamic images by X- and Y-like cells, to assess the health of the Y-like cells without effects of the X-like cells.

The different dynamic images may provide perceptions of features having at least one of varying orientations and spacing when processed by Y-like cells and the patient input may identify at least one of a perceived feature orientation and spacing of given displayed dynamic image. In turn, the controller may vary at least one of the feature orientation and spacing of successive dynamic images and compares corresponding patient input to assess the functioning of Y-like cells in different portions of the retina corresponding to the different visual field locations.

It is thus a feature of at least one embodiment of the invention to provide an easily identifiable stimulus pattern that may be discerned using peripheral as well as central vision and thus is suitable for glaucoma testing and tracking disease progression.

Alternatively, or in addition, the dynamic images may provide perception of motion when received by the Y-like cells and wherein the controller varies at least one of speed and direction of the motion in successive dynamic images and the patient input identifies a corresponding one of at least speed and direction of motion in the dynamic images and wherein the controller compares corresponding patient input to assess the functioning of Y-like cells in different portions of the retina corresponding to the different visual field locations.

It is thus a feature of at least one embodiment of the invention to provide different options for dynamic images that are sensitive to Y-like cell health that may be used alternatively or in addition to provide improved clinical sensitivity and specificity for given patients.

The perceptions may be derived from fine-grain texture-like features of the dynamic images having a relatively high spatial frequency of 1.0 to 20.0 cycles per degree, which are static or moving or dynamically modulated at a temporal frequency up to 30 cycles per second.

It is thus a feature of at least one embodiment of the invention to provide fine resolution and rapidly changing dynamic images that are substantially featureless when processed by X-like cells, but which are perceptually visible when processed by Y-like cells and in this way make it easier for the patient to make accurate pattern assessments, distinguishing a pattern from a featureless or nearly featureless display compared to distinguishing two different bar patterns.

In one embodiment, the dynamic images may provide a spatiotemporal pattern of intensity following an amplitude modulation of a carrier pattern, the latter of which alone is imperceptible to the patient.

It is thus a feature of at least one embodiment of the invention to provide a contrast modulated signal that can reveal nonlinear downstream processing uniquely dependent on signals from Y-like cells.

The electronically controllable display may provide a center fixation target for the patient to focus on during the test and wherein the locations of the dynamic images are arranged at varying distances and angles about the fixation target, and an eye movement monitoring device to verify that the patient's gaze is directed to the fixation target.

It is thus a feature of at least one embodiment of the invention to provide an apparatus that can be used as a replacement for a current, well understood automated perimetry device that is conventionally used to test for glaucoma.

The electronically controllable display may include a digital light projector (DLP) using micromirrors, and providing a refresh rate of at least 100 hertz, and projecting on a screen viewable by the patient.

It is thus a feature of at least one embodiment of the invention to provide an electronically controllable display that can produce high resolution, high contrast, and high frame rate dynamic images suitable for the present invention. It is another object of the invention to provide an electronic display providing a well-characterized linear relationship between the control signal and image intensity, eliminating the need for gamma correction or the like to compensate for display device nonlinearity.

The controller may vary at least one of contrast and size of the dynamic images according to the location of the stimulus with respect to the fixation target.

It is thus a feature of at least one embodiment of the invention to account for normal variations in the contrast sensitivity and size-scaling of retinal cells as a function of distance from the fovea, and to allow adjustment of the apparatus for variations between different individuals.

These particular objects and advantages may apply to only some embodiments falling within the claims and thus do not define the scope of the invention.

DETAILED DESCRIPTION OF THE PREFERRED EMBODIMENT

Figure 1:
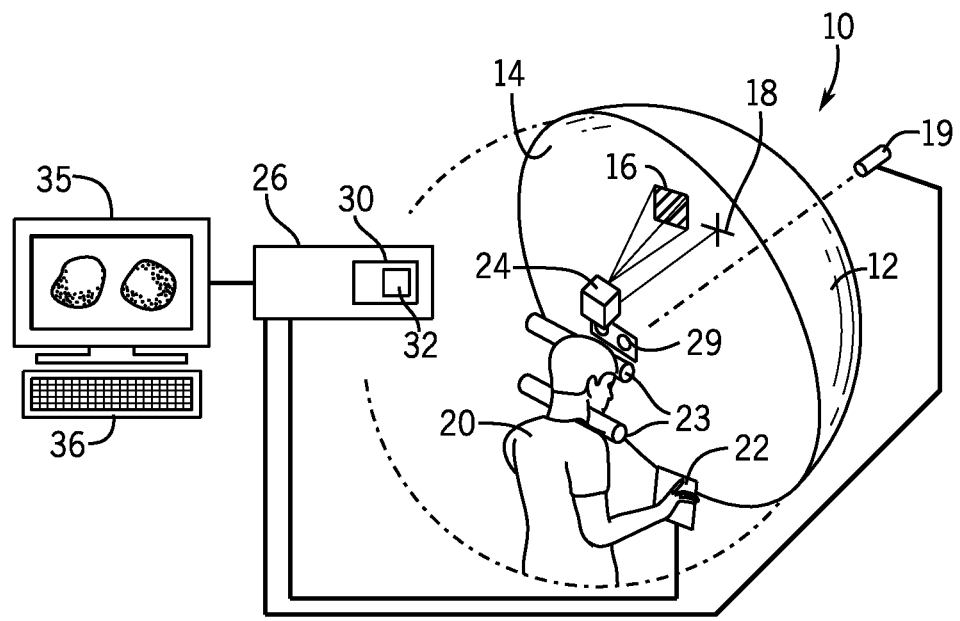
FIG. 1 is a simplified perspective view of an automated perimetry system incorporating the present invention and showing a projector under the control of a programmable controller system for projecting Y-like cell specific dynamic images on a screen viewed by a patient.

Referring now to FIG. 1, a glaucoma detection apparatus 10 constructed according to one embodiment of the present invention may provide for a hemispherical screen 12 having an inner reflective surface 14 onto which a dynamic image pattern 16 and center fixation target 18 may be projected. The hemispherical screen 12 may be positioned with respect to a patient 20 to substantially subtend the field of view of the patient 20 when the patient 20 has his or her eyes fixed on the center fixation target 18. In this respect the hemispherical screen 12 may be a portion of a sphere centered at a location near the patient's eyes. An eye tracking camera 19 may be positioned to focus on the patient's eye that is to be tested, to determine times when the patient 20 is viewing the center fixation target 18 as will be discussed below.

The patient 20 may rest his or her head against a head and chin rest 23 to help stabilize the patient's head. The chin rest 23 will have two positions, for the patient 20 to use one or the other of, to test either the left or right eye of the patient 20 for separate testing of each eye, with the other eye being occluded. In this regard, the head and chin rest 23 will include spectacle lenses 29 to bring the patient's eyes into focus on the displayed fixation target 18. A response device 22 such as a button box, keypad, or other hardware input device, may be provided to the patient 20 to receive patient input describing a perception of the patient 20 of the dynamic images 16 viewed by the patient using the patient's central or peripheral vision. The response device 22 may, for example, allow the patient 20 to distinguish between orientation, motion, motion direction, motion speed, and pattern coarseness of the dynamic image 16 as will be discussed below.

The dynamic images 16 may be presented by a projector 24 at a series of sequentially different locations on the hemispherical screen 12 about the center fixation target 18, the latter of which is desirably fixed in position at a center point on the hemispherical screen 12.

The projector 24 and response device 22 communicate with a programmable controller 26, for example a micro-computer or FPGA (field programmable gate array) or the like, communicating with an electronic memory 30 holding a program 32 as will be discussed below. The programmable controller 26 may further provide for the operator, a display screen 35, for example, a standard LCD computer display, and operator input devices 36 such as a keyboard, a mouse or the like for providing inputs to the program 32.

Figure 2:
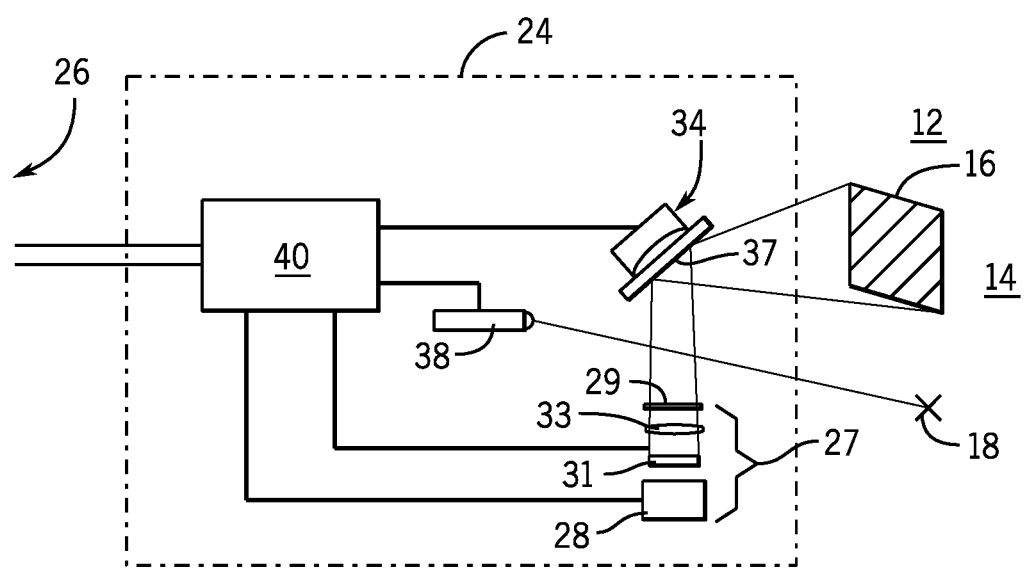
FIG. 2 is a block diagram of the projector of FIG. 1 providing a high-resolution dynamic image at various locations in the periphery of the patient's vision, and a fixation target projector providing a central fixation target.

Referring also to FIG. 2, the projector 24 may provide a graphic image projector assembly 27 allowing the projection of a high-resolution two-dimensional dynamic image 16 with a spatial resolution viewed by the patient 20 (measured along two orthogonal directions) sufficient to render spatial frequencies of at least 20 cycles per degree, and with a refresh rate of at least 100 frames per second. In this regard, the graphic image projector assembly 27 may include a collimated light source 28 (for example, an LED array) whose light is modified by a digital light processor (DLP) mirror array 31. The DLP mirror array 31 provides an array of micro mirrors that can be switched rapidly between on and off states as is generally understood in the art to provide highly linear control of the illumination of each pixel of a dynamic image by control of duty cycle modulation of the mirrors. Light modified by the DLP mirror array 31 is focused by focusing optics 33 (set to provide focused dynamic images 16 on the hemispherical screen 12). Light from the focusing optics 33 is then reflected off of a front surface mirror 37 of a pair of mirror galvanometers 34 that may steer the location of the dynamic image 16 to a variety of locations over a majority of the surface 14 of the hemispherical screen 12 by orthogonal deflections of the front surface mirror 37.

The fixation point projector 38 may include a laser pointer or other such device for producing a simple static image to serve as the center fixation target 18 (for example, in the form of concentric circles or a letter such as an "E") and may provide for mechanical adjustment together with other elements of the projector 24 to locate the center fixation target 18 at the center of the hemispherical screen 12 while providing a known relationship between the center of the hemispherical screen 12 and each location of a dynamic image 16.

Each of the servo controller 40, light source 28, DLP mirror array 31, and laser pointer 38 may be actuated by a programmable controller device 26 incorporating an electronic interface that allows the projector 24 to receive from the programmable controller 26 image data to generate the dynamic image 16 by control of the DLP mirror array 31. A servo-controller 40 may also receive from the programmable controller 26 location data for the dynamic image to control the mirror galvanometer 34 and hence the position of the dynamic image 16.

Figure 3:
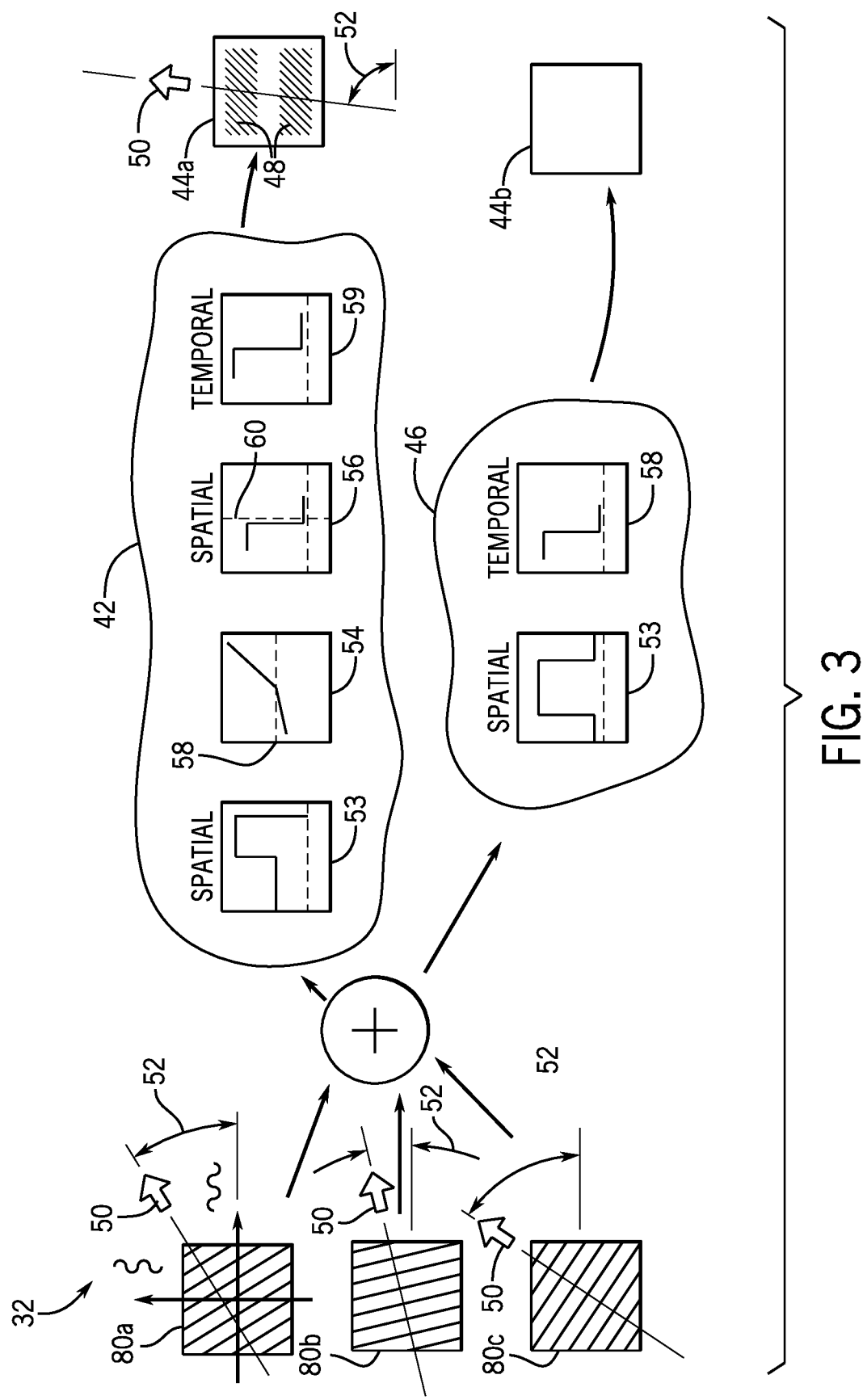
FIG. 3 is a flow diagram of the process of generating Y-like cell specific dynamic images by the programmable controller in FIG. 1.

Referring now to FIG. 3, generally the program 32 executing on the programmable controller 26 will generate a dynamic image 16 such that the resulting percept 44a or 44b (perceived images by the patient 20) differs according to whether the dynamic images 16 are processed by the Y-like cells 42 or the X-like cells 46. In particular, the patient's percept of the dynamic images 44a processed by the Y-like cells 42 may show a series of stripes 48, either stationary or having a drift direction and speed 50 at an orientation angle 52. More generally, the stripes 48 may be other coarse-scale features such as bars, edges, discs, or the like. The periodicity of the stripes 48, their drift direction and speed 50, and their orientation angle 52 may be adjusted (as will be discussed below) by the programmable controller 26. In contrast, the patient's percept of the dynamic images 44b processed by the X-like cells 46 may have no perceived stripes 48 or exhibit the stripes 48 in extremely attenuated form to be practically imperceptible to the extent that it can be readily distinguished from the percept 44a (perceived images by the patient 20).

While the inventors do not wish to be bound by a particular theory, this difference in perceived dynamic images 44a and 44b is believed to be the result of a nonlinearity in the processing of the dynamic image 16 by the Y-like cells 42 that does not occur to a substantial degree in the processing performed by the X-like cells 46. In this respect, the processing of the Y-like cells 42 may be modeled as providing a spatial bandpass filter 53 followed by a nonlinearity such as a rectification function 54 followed by a spatial low-pass filter function 56 having cutoff frequency 60 and a temporal low-pass filter 59. For example, a rectification function 54 provides relatively high-gain mapping between luminance values and Y-like cell 42 output response when the received luminance is above a nonzero luminance threshold 58. Luminance values below this luminance threshold 58 are largely attenuated with a low-gain mapping in the manner of a rectifier.

Consider now the situation where the dynamic image 16 has a high spatial frequency and high temporal frequency "carrier signal", and a low spatial frequency and low temporal frequency envelope modulation of that high frequency carrier. The spatial bandpass filter 53 allows passage of this high spatial frequency carrier which is then received by the rectification function 54. The rectification function 54 essentially demodulates the carrier to produce a low spatial frequency and low temporal frequency signal at the envelope frequencies in addition to the high spatial frequency carrier signal. The spatial low-pass filter function 56 and temporal low-pass filter function 59 block the carrier signal but allow the low-frequency envelope signal having low spatial frequency and low temporal frequency to be passed as stripes 48 or other features.

In other words, the result of the rectification function 54 and the low-pass filter functions 56 and 59 is that an "envelope" of a contrast modulated dynamic image 16 will be extracted, or demodulated, by the Y-like cells 42 while the underlying carrier signal is blocked. This effect is obtained in any image that can be characterized as "non-Fourier" or "second order", that is, images having fine spatial scale features whose spatial variation are revealed only by a nonlinearity, in the retinal cells that "demodulate" the stimulus, such a nonlinearity being in contrast to the linear superposition that characterizes Fourier decomposition.

In contrast to the Y-like cells 42, the X-like cells 46 are believed not to have the nonlinearity of the rectification function 54 to a significant degree and have spatial bandpass filter functions 53 shifted to higher spatial frequencies, and temporal low-pass filter functions 59. As a result, there is no demodulated envelope that can be passed by the low-pass filter 59 yet again the "carrier" frequency of the dynamic images 16 is blocked or highly attenuated resulting in a practically featureless percept 44b. Importantly, even if perceptible, the carrier will be distinguishable from the percept 44a so there is low risk that viewing of the carrier will be confused with being able to view the percept 44a.

The spatial and temporal sensitivities of the Y-like cells 42 and X-like cells 46, and nonlinearities of the Y-like cells 42, act so that the lower temporal and spatial frequency stripes 48 of dynamic percept 44a and 44b are more pronounced perceptually than the spatially fine-grain features of the dynamic image 16.

In one example, a set of dynamic images 16 may be generated from the sum of three different two-dimensional sinusoidal fields 80a, 80b, and 80c each having an independently controllable spatial frequency, orientation angle 52, and drift direction and speed 50 orthogonal to that orientation. The sum of these fields may be expressed by the equation:

$$I(x,y,t) = \cos(\omega_C \cdot [x,y,t]) + 0.5 \cdot \{\cos([\omega_C - \omega_E] \cdot [x,y,t]) + \cos([\omega_C + \omega_E] \cdot [x,y,t])\} \quad (1)$$

where I is intensity at a pixel,

[x, y, t] is a vector describing the Cartesian location and time of the pixel, $\omega_C$ is a vector defining a "carrier" spatial and temporal frequency (having x- and y-components that define the orientation angle 52 and the time component describing the drift direction and speed 50) and, $\omega_E$ is a vector describing the spatial and temporal "modulating" frequency.

The three terms to the right side of equation (1) that sum together to define the intensity are represented by 80a, 80b, and 80c as shown in FIG. 3. Field 80a may be interpreted as a carrier sinusoidal field $\cos(\omega_C \cdot [x, y, t])$ and fields 80b and 80c that represent a multiplication between the carrier $\cos(\omega_C \cdot [x, y, t])$ and the modulating frequency $\cos(\omega_E \cdot [x, y, t])$ converted to a summation by a trigonometric identity for ease of processing. Generally, it will be understood that the drift direction and speed 50 and orientation angle 52 of the stripes 48 may be easily controlled by adjusting the vectors $\omega_C$ and $\omega_E$ in the program 32.

The dynamic images 16 are, in their most general form, produced by any spatially fine-grain, texture-like dynamical pattern, the "carrier", whose contrast is modulated by a more coarse-grain pattern, the "envelope", as follows:

$$I(x,y,t) = I_0 + \text{Carr}([x,y,t])[1 + \text{Env}([x,y,t])]$$

where I(x, y, t) is the luminance intensity of a pixel at spatial location (x,y) at time t, $I_0$ is the space- and time-average luminance of the spatiotemporal pattern I(x, y, t),

[x,y,t] is a vector describing the Cartesian location and time of the pixel,

Carr is a 3d zero-mean matrix defining a "carrier" pattern as a function of spatial location [x,y] and time [t] and, Env is a 3d zero-mean matrix defining an "envelope" pattern as a function of spatial location [x,y] and time [t], that "modulates" the amplitude of the carrier.

Referring still to FIG. 3, the dynamic images 16 may be generated procedurally by the programmable controller 26, for example, by generating a three-dimensional sinusoidal variation in image intensity where that sinusoidal variation is modulated by multiplication with a second three-dimensional sinusoid. For example, in one embodiment, a dynamic image 16 may be generated from a carrier pattern that may be a drifting sinewave grating with a high spatial frequency and high temporal frequency, and an envelope pattern which may be a drifting sinewave grating with a low spatial frequency and low temporal frequency, the carrier and envelope patterns having independently controllable spatial frequency, orientation angle 52, and drift direction and speed 50. The resultant dynamic image may be expressed by the equations:

$$\text{Carr}(x,y,t) = C_c \cos(\omega_C \cdot [x,y,t])$$

where Carr([x,y,t]) is the spatiotemporal carrier pattern (as above)

[x,y,t] is a vector describing the Cartesian location and time of the pixel, $C_c$ is the amplitude of the carrier sinewave grating $\omega_C$ is a vector defining a "carrier" spatial and temporal frequency (having x- and y-components that define the orientation angle 52 and the time component describing the drift direction and speed 50)

$$\text{Env}(x,y,t) = C_e \cos(\omega_e \cdot [x,y,t])$$

where Env(x,y,t) is the spatiotemporal envelope ("modulating") pattern (as above)

[x,y,t] is a vector describing the Cartesian location and time of the pixel, $C_e$ is the Michelson contrast (0.0 to 1.0), or "modulation depth", of the envelope sinewave grating $\omega_C$ is a vector defining an "envelope" spatial and temporal frequency (having x- and y-components that define the orientation angle 52 and the time component describing the drift direction and speed 50)

Generally, it will be understood that the envelope modulation depth $C_e$, orientation angle $\theta_e$ 52, direction of motion, spatial frequency, and temporal frequency of the envelope pattern (sinusoidal stripes) 48, as well as the carrier amplitude, orientation angle stripes, direction of motion, spatial frequency, and temporal frequency will be easily controlled by adjusting the parameters in the controller program 32. It will be generally understood that temporal frequency may be considered separately from direction of motion (where the temporal frequency is positive only) or may subsume direction of motion by considering direction of motion to be defined by positive and negative values of temporal frequency.

Figure 4:
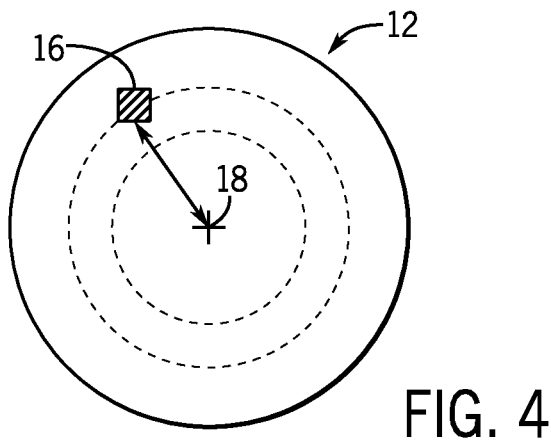
FIG. 4 is a front elevational view of the screen of FIG. 1 showing the location of a Y-like cell-specific dynamic image with respect to a screen center such as can be used to control contrast and size-scaling of the dynamic images.

Referring now to FIG. 4, the present invention also contemplates that the contrast and/or size-scaling of the dynamic image 16 may be adjusted as a function of its distance from the center fixation target 18, for example, to compensate for known variations in the sensitivity of retinal cells, as well as normal variations between individuals, not necessarily associated with glaucoma.

Figure 5:
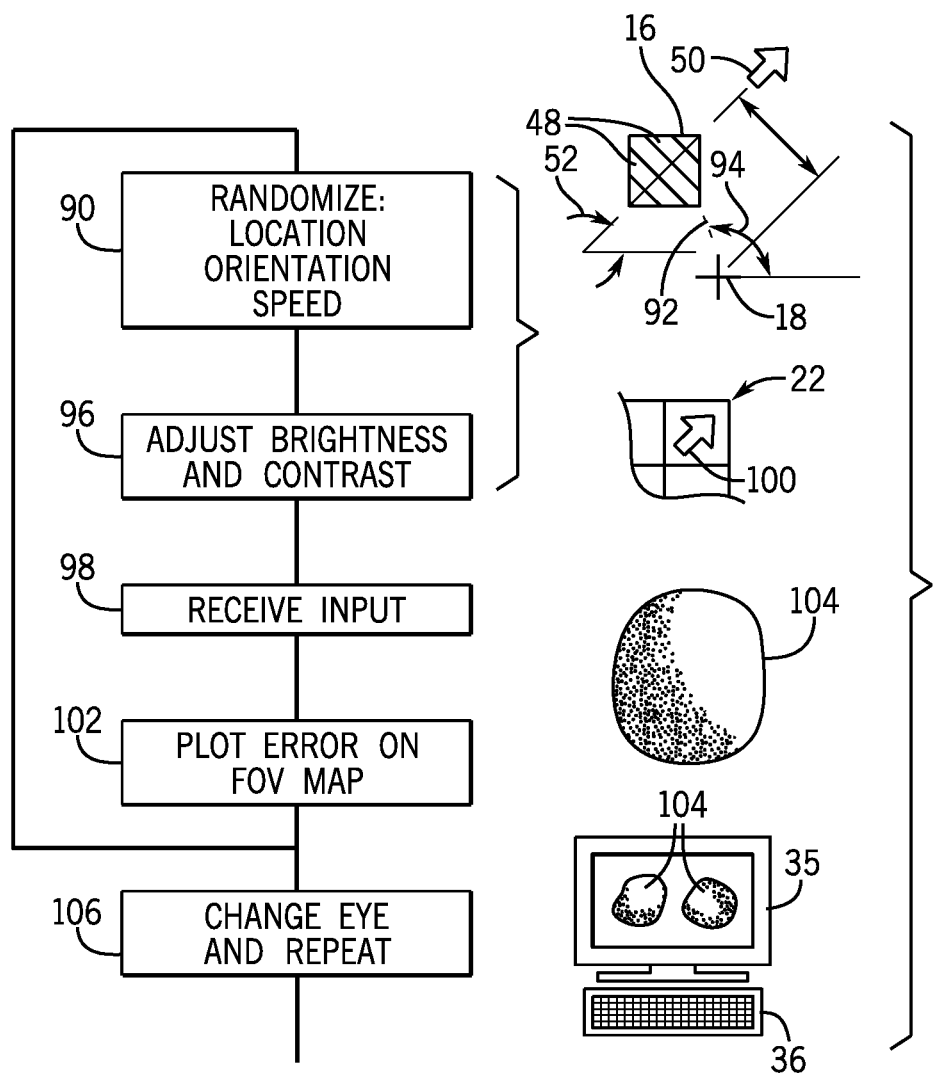
FIG. 5 is a flowchart of the program executed by the electronic programmable controller of FIG. 1 during a glaucoma screening test.

Referring now to FIG. 5 as well as FIGS. 3 and 4, the program 32 of the programmable controller 26 may operate repeatedly to randomize a location being a distance 92 and angle 94 of a dynamic image 16 generated as discussed above with respect to the center fixation target 18. Each successive, presented dynamic image 16 may have a different orientation 52 and/or drift direction and/or speed 50 so as to generate perceived stripes 48 in the dynamic image 16 that will have different perceivable orientations or different stripe motions per process block 90. In this process block 90, the envelope contrast or carrier amplitude can also be varied on successive trials to change the level of difficulty of perceptual judgment.

Optionally, per process block 96, adjustment of size-scaling or contrast of the dynamic image 16 may be made based on the distance 92 and/or a combination of distance 92 and angle 94 as discussed above.

At process block 98, the programmable controller 26 may receive an input from the patient 20, for example, using the response device 22 indicating direction and/or speed and/or orientation and/or spacing of the perceived stripes 48, for example, through arrow, letter or number labels 100 on the various buttons or keys of the response device 22 indicating motion, direction, speed, and orientation. This input may be tested to see if the patient 20 has their eyes fixed on the fixation target 18 using the eye tracking camera 19 and may be discounted or uncounted if not. In addition, the process of process blocks 90, 96, 98, 102, and 106 may initiate only after the patient has eyes fixed on the fixation target 18. The period of time for receiving the input per process block 98 may be limited to a predetermined window after placement of the dynamic image 16.

At process block 102, a determination is made as to whether the direction and/or speed and/or orientation and/or spacing of the perceived stripes 48 identified by the patient per process block 98 match the actual stripes 48 generated per process block 90 and 96. Whether the matching is correct or in error, across the ensemble of tests in different visual field locations, is used to construct the field-of-view map 104 showing schematically the patient's field-of-view for one of the left or right eye. This field-of-view map 104 may show a density of errors in identification of the stripes 48 by the patient 20 in corresponding to the locations of the dynamic images 16 invoking the error, and in this respect shows loss of Y-like cells 42 in the patient's retina responsible for representing those areas of the field-of-view. Successive field-of-view maps 104 taken over time (typically many days, weeks, months, and/or years) can provide a sensitive indication of progression of glaucoma. When the level of difficulty of the tests is varied, this information may be used to weight the assessment of whether the patient has correctly identified the stripes 48 and thus to provide a more nuanced output in the field-of-view map 104.

This sequence of process blocks 90, 96, 98, and 102 may be repeated for a desired number of dynamic images 16 needed to build up a detailed field-of-view map 104. At process block 106, the patient 20 may change eyes being tested by changing position on the chin rest, and thereby which eye is occluded, as discussed above. For each different eye, the sequence of process blocks 90, 96, 98, and 102 is repeated.

At the conclusion of this testing of each eye, a pair of field-of-view maps 104 may be displayed together with analysis, for example, quantifying the usable field-of-view of the patient, for example, which is helpful in making longitudinal comparisons of these changes over time. Other types of displays commonly obtained with automated perimetry can be duplicated with the additional specificity obtained by isolation of the Y-like cells, providing advanced indication of cell death.

As used herein, "Y-like cell" shall be understood to be "parasol retinal ganglion cells" or "smooth retinal ganglion cells", or "upsilon retinal ganglion cells" as is understood in the art and "X-like cell" shall be understood to be "midget retinal ganglion cells" as is also understood in the art.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a controller" and "a processor" or "the microprocessor" and "the processor," can be understood to include one or more microprocessors, FPGAs (field programmable gate arrays) that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

To aid the Patent Office and any readers of any patent issued on this application in interpreting the claims appended hereto, applicants wish to note that they do not intend any of the appended claims or claim elements to invoke 35 U.S.C. 112(f) unless the words "means for" or "step for" are explicitly used in the particular claim.

What we claim is:

1. An apparatus for glaucoma and retinal diseases diagnosis comprising:
   an electronically controlled dynamic image display adapted for viewing by a human patient;
   a display driver for generating a series of dynamic images presentable on the electronically controlled display, each dynamic image providing a distinguishably different perception when received by only X-like cells than when received by Y-like cells;
   a patient input device for receiving a patient input describing orientation or direction of motion of a perceived pattern in the series of dynamic images displayed on the electronically controlled display; and
   a controller communicating with the display driver and electronically controlled display to:
   (1) display different dynamic images at different locations within a field-of-view of a patient viewing the electronically controllable display; and
   (2) analyze the patient input for the different locations of each of the dynamic images to assess a loss of Y-like cells in different portions of the retina corresponding to the different locations.

2. The apparatus of claim 1 wherein the perceptions of the dynamic image result from a nonlinearity in a processing of the dynamic image by the Y-like cells and not by the X-like cells.

3. The apparatus of claim 1 wherein the different dynamic images provide perceptions of stripes having at least one of varying orientations and spacing when processed by Y-like cells and wherein the patient input identifies at least one of a perceived stripe orientation and spacing of given displayed dynamic image and wherein the controller varies at least one of the stripe orientation and spacing of successive dynamic images and compares corresponding patient input to assess the functioning of Y-like cells in different portions of the retina corresponding to the different locations.

4. The apparatus of claim 1 wherein the dynamic images provide a perception of motion when received by the Y-like cells and wherein the controller varies at least one of speed and direction of the motion in successive dynamic images and the patient input identifies a corresponding one of at least speed and direction of motion in the dynamic images and wherein the controller compares corresponding patient input to assess the functioning of Y-like cells in different portions of the retina corresponding to the different locations.

5. The apparatus of claim 1 wherein the perceptions are derived from features of the images having a spatial frequency of greater than 1 cycles per degree and have a spatial frequency of less than 20 cycles per degree.

6. The apparatus of claim 1 wherein the perceptions are derived from features of the images having a temporal frequency magnitude of less than 30 cycles per second.

7. The apparatus of claim 1 wherein the images provide a spatiotemporal pattern of intensity following an amplitude modulation of a carrier pattern, the latter of which is distinguishably different from the perception resulting from processing of the Y-like cells.

8. The apparatus of claim 1 wherein the electronically controllable display provides a center fixation target for the patient to focus on during use of the apparatus and wherein the locations of the images are arranged at varying distances and angles about the fixation target.

9. The apparatus of claim 1 wherein the electronically controllable display includes a digital light projector using micromirrors and provides a refresh rate of at least 100 hertz and projects on a screen viewable by the patient.

10. The apparatus of claim 1 wherein the controller varies at least one of contrast and size-scaling of the images according to the location of the image with respect to a predetermined center of the electronically controllable display.

11. The apparatus of claim 1 further including a head support stabilizing the patient's head and occluders for alternatively blocking the left or right eye of the patient.

12. A method of glaucoma and retinal diseases diagnosis comprising:
(a) displaying a series of dynamic images on an electronically controlled display at different locations within a field-of-view of a patient viewing the electronically controllable display, each dynamic image providing a distinguishably different perception when processed by only X-like cells than when processed by Y-like cells;
(b) receiving patient input describing orientation or direction of motion of a perceived pattern in the dynamic images displayed on the electronically controlled display; and
(c) analyzing the patient input and location of each of the dynamic images to assess a loss of Y-like cells in different portions of the retina corresponding to the different locations.

13. The method of claim 12 wherein the perceptions of the dynamic images result from a nonlinearity in a processing of the dynamic images by the Y-like cells and not by the X-like cells.

14. Method of claim 12 wherein the different dynamic images provide perceptions of stripes having at least one of varying orientations and spacing when processed by Y-like cells and wherein the patient input identifies at least one of a perceived stripe orientation and spacing of given displayed dynamic image and wherein the controller varies at least one of the stripe orientation and spacing of successive dynamic images and compares corresponding patient input to assess the functioning of Y-like cells in different portions of the retina corresponding to the different locations.

15. The method of claim 12 wherein the dynamic images provide a perception of motion when received by the Y-like cells and wherein the controller varies at least one of speed and direction of the motion in successive dynamic images and the patient input identifies a corresponding one of at least speed and direction of motion in the dynamic images and wherein the controller compares corresponding patient input to assess the functioning of Y-like cells in different portions of the retina corresponding to the different locations.

16. The method of claim 12 wherein the perceptions are derived from features of the images having a spatial frequency of greater than 1 cycles per degree and have a spatial frequency of less than 20 cycles per degree.

17. The method claim 12 wherein the perceptions are derived from features of the images having a temporal frequency magnitude of less than 30 cycles per second.

* * * * *